(12) United States Patent
Keitel et al.

(10) Patent No.: US 8,747,367 B2
(45) Date of Patent: Jun. 10, 2014

(54) INJECTION DEVICE

(75) Inventors: Joachim Keitel, Esslingen (DE); Jochen Gabriel, Stuttgart (DE)

(73) Assignee: Haselmeier GmbH, St. Gallen (CH)

( * ) Notice: Subject to any disclaimer, the term of this patent is extended or adjusted under 35 U.S.C. 154(b) by 683 days.

(21) Appl. No.: 10/549,004

(22) PCT Filed: Jul. 28, 2004

(86) PCT No.: PCT/EP2004/008422
§ 371 (c)(1),
(2), (4) Date: Sep. 14, 2005

(87) PCT Pub. No.: WO2005/046770
PCT Pub. Date: May 26, 2005

(65) Prior Publication Data
US 2006/0258988 A1 Nov. 16, 2006

(30) Foreign Application Priority Data
Nov. 3, 2003 (DE) .............................. 203 17 377 U

(51) Int. Cl.
*A61M 5/00* (2006.01)
(52) U.S. Cl.
USPC ....................................................... 604/211
(58) Field of Classification Search
USPC ................. 604/191, 181, 82, 207–211, 187
See application file for complete search history.

(56) References Cited

U.S. PATENT DOCUMENTS

| | | | | |
|---|---|---|---|---|
| 4,194,505 A * | 3/1980 | Schmitz | .......................... | 604/138 |
| 4,973,318 A | 11/1990 | Holm et al. | .................... | 604/208 |
| 5,092,842 A * | 3/1992 | Bechtold et al. | ............... | 604/135 |
| 5,104,380 A * | 4/1992 | Holman et al. | ................ | 604/117 |
| 5,114,406 A * | 5/1992 | Gabriel et al. | ................. | 604/136 |
| 5,226,896 A | 7/1993 | Harris | ............................ | 604/211 |
| 5,271,527 A * | 12/1993 | Haber et al. | ..................... | 222/43 |
| 5,295,976 A * | 3/1994 | Harris | ............................ | 604/211 |
| 5,320,609 A | 6/1994 | Haber et al. | ................... | 604/135 |
| 5,383,865 A | 1/1995 | Michel | ........................... | 604/232 |
| 5,480,387 A * | 1/1996 | Gabriel et al. | ................. | 604/134 |
| 5,505,704 A * | 4/1996 | Pawelka et al. | ............... | 604/191 |
| 5,562,616 A * | 10/1996 | Haber et al. | ..................... | 604/82 |
| 5,584,815 A * | 12/1996 | Pawelka et al. | ............... | 604/191 |
| 5,591,136 A | 1/1997 | Gabriel | ......................... | 604/211 |
| 5,626,566 A | 5/1997 | Petersen et al. | ............... | 604/208 |

(Continued)

FOREIGN PATENT DOCUMENTS

| | | |
|---|---|---|
| AU | 2003-213971 A | 10/2003 |
| DE | 41 12 259 | 10/1992 |

(Continued)

*Primary Examiner* — Bhisma Mehta
*Assistant Examiner* — Bradley Osinski
(74) *Attorney, Agent, or Firm* — Milton Oliver, Esq.; Oliver Intellectual Property LLC

(57) ABSTRACT

An injection apparatus has a barrel (50) that is adapted to receive a container (108) with injection fluid (110). It further comprises a piston rod (98), provided with a thread (100), for expelling injection fluid (110) from such a container (108), which piston rod (98) is guided relative to the barrel (50) in the axial direction (112, 114). Additionally provided is a threaded part (122) whose thread (120) is in engagement with the thread (100) of the piston rod (98), which threaded part (122) is rotatable relative to the piston rod (98) and relative to the barrel (50) in order to set an injection dose, and, during an injection operation, is prevented from rotating relative to the piston rod (98).

28 Claims, 19 Drawing Sheets

(56) References Cited

U.S. PATENT DOCUMENTS

| | | | |
|---|---|---|---|
| 5,679,111 A * | 10/1997 | Hjertman et al. | 604/135 |
| 5,938,642 A * | 8/1999 | Burroughs et al. | 604/208 |
| 5,944,700 A * | 8/1999 | Nguyen et al. | 604/263 |
| 5,957,896 A | 9/1999 | Bendek et al. | 604/207 |
| 6,001,089 A * | 12/1999 | Burroughs et al. | 604/506 |
| 6,004,297 A | 12/1999 | Steenfeldt-Jensen | 604/207 |
| 6,048,336 A * | 4/2000 | Gabriel | 604/211 |
| 6,228,067 B1 * | 5/2001 | Gabriel | 604/211 |
| 6,235,004 B1 | 5/2001 | Steenfeldt-Jensen | 604/207 |
| 6,241,709 B1 | 6/2001 | Bechtold et al. | 604/207 |
| 6,290,679 B1 * | 9/2001 | Hostettler et al. | 604/208 |
| 6,413,242 B1 * | 7/2002 | Michel et al. | 604/187 |
| 6,485,470 B2 * | 11/2002 | Hostettler et al. | 604/208 |
| 6,663,602 B2 | 12/2003 | Moller | 604/211 |
| 6,796,970 B1 * | 9/2004 | Klitmose et al. | 604/207 |
| 6,899,699 B2 * | 5/2005 | Enggaard | 604/246 |
| 7,000,656 B2 * | 2/2006 | Todd | 141/180 |
| 7,112,187 B2 * | 9/2006 | Karlsson | 604/187 |
| 2002/0052578 A1 * | 5/2002 | Moller | 604/208 |
| 2002/0120235 A1 * | 8/2002 | Enggaard | 604/135 |
| 2002/0151855 A1 * | 10/2002 | Douglas et al. | 604/218 |
| 2003/0187405 A1 | 10/2003 | Gatti et al. | 604/207 |
| 2004/0133163 A1 | 7/2004 | Schiffmann | 604/131 |
| 2004/0186431 A1 | 9/2004 | Graf et al. | 604/124 |
| 2004/0186441 A1 | 9/2004 | Graf et al. | 604/124 |
| 2004/0186442 A1 | 9/2004 | Graf et al. | 604/124 |
| 2004/0215152 A1 | 10/2004 | Kirchhofer et al. | 604/211 |
| 2004/0215153 A1 | 10/2004 | Graf et al. | 604/124 |
| 2005/0165363 A1 | 7/2005 | Judson et al. | 604/209 |
| 2006/0206057 A1 | 9/2006 | DeRuntz et al. | 604/224 |
| 2006/0258988 A1 * | 11/2006 | Keitel et al. | 604/181 |

FOREIGN PATENT DOCUMENTS

| | | |
|---|---|---|
| DE | 694 20 297 T2 | 9/1994 |
| DE | 699 00 026 T2 | 8/1999 |
| DE | 100 47 637 | 4/2002 |
| DE | 101 29 585 | 1/2003 |
| EP | 0 327 910 A2 | 8/1989 |
| EP | 0 897 728 | 2/1999 |
| EP | 12 28 777 A1 | 8/2002 |
| EP | 1 656 170 A1 | 5/2006 |
| WO | WO 99-38554 | 8/1999 |
| WO | WO 00-41754 | 7/2000 |
| WO | WO 01-95959 A1 | 12/2001 |
| WO | WO 03-011370 A2 | 2/2003 |
| WO | WO 03/011374 A1 | 2/2003 |
| WO | WO 03-080160 A1 | 10/2003 |
| WO | WO 03/086512 A | 10/2003 |
| WO | WO 2005-018721 A1 | 3/2005 |

* cited by examiner

INJECTION DEVICE

CROSS-REFERENCE

This application is a section 371 of PCT/EP2004/008422, filed Jul. 28, 2004, claiming priority from German application DE 203 17 377.5, filed Nov. 3, 2003, the entire content of which is hereby incorporated by reference.

FIELD OF THE INVENTION

The invention concerns an injection apparatus in which a piston rod is guided in the axial direction.

BACKGROUND

With injection apparatuses, it is desirable for their operation to be easily understandable, i.e. intuitive, and for the patient to have good control over the injection operation, i.e. to be able to understand what is happening.

SUMMARY OF THE INVENTION

It is therefore an object of the invention to make a new injection apparatus available.

According to the invention, this object is achieved by an injection apparatus in which a barrel holds a container of injectable fluid, and a threaded part is in engagement with a thread on a piston rod, the threaded part being rotatable during a dose-setting operation but not during an injection operation driven by the piston rod.

Before an injection, the patient sets a desired injection dose by rotating the threaded part relative to the piston rod and relative to the barrel, the threaded part being displaced axially relative to the piston rod and relative to the barrel.

After insertion of the needle, the patient then performs the injection, the threaded part being displaced axially in the injection direction relative to the barrel and moving together with the piston rod, i.e. not performing a relative motion relative to the latter, since it is prevented from rotating relative to it.

A sophisticated interplay of rotary motions and axial motions is thus used on the one hand to set the dose, and on the other hand to inject the previously set dose after the setting operation. Operation in this manner is intuitively easy to understand.

If the patient has inadvertently set the dose too high, he can reduce it again. With an apparatus according to the invention, this "dose correction" is just as simple as setting the dose itself, and is easy to understand.

Further details and advantageous refinements of the invention are evident from the exemplary embodiments, in no way to be understood as a limitation of the invention, that are described below and depicted in the drawings.

BRIEF FIGURE DESCRIPTION

DETAILED DESCRIPTION

Figure 1:
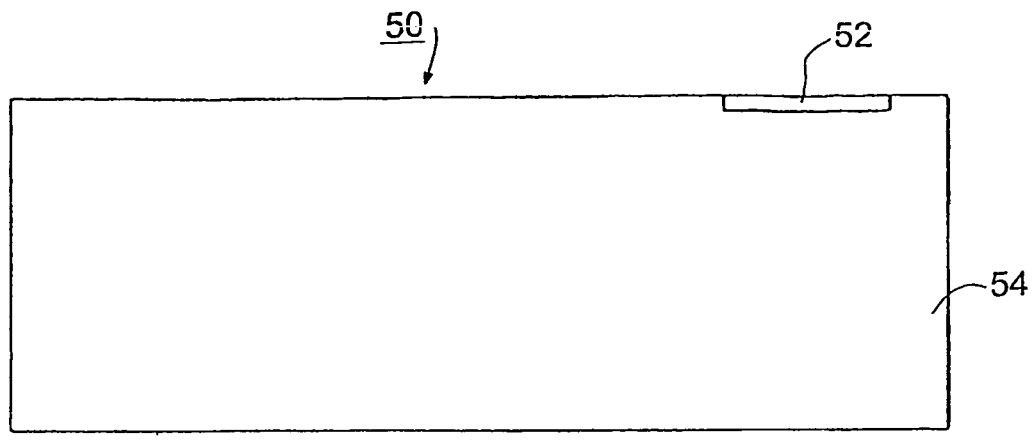
FIG. 1 is a side view of the barrel of an injection apparatus according to a preferred embodiment of the invention.

The description below first explains the general construction and mode of operation of the invention with reference to greatly enlarged and schematized depictions. That is followed by a specific exemplary embodiment in the form of a so-called "pen injector." In the description, the same reference characters are used in each case for identical or identically functioning parts, and those parts are usually described only once.

Directions of motion are indicated in the manner usual in medicine, i.e.

proximal=toward the patient, i.e. in the direction toward the injection needle;

distal=away from the patient, i.e. in the direction away from the injection needle.

Figure 12:
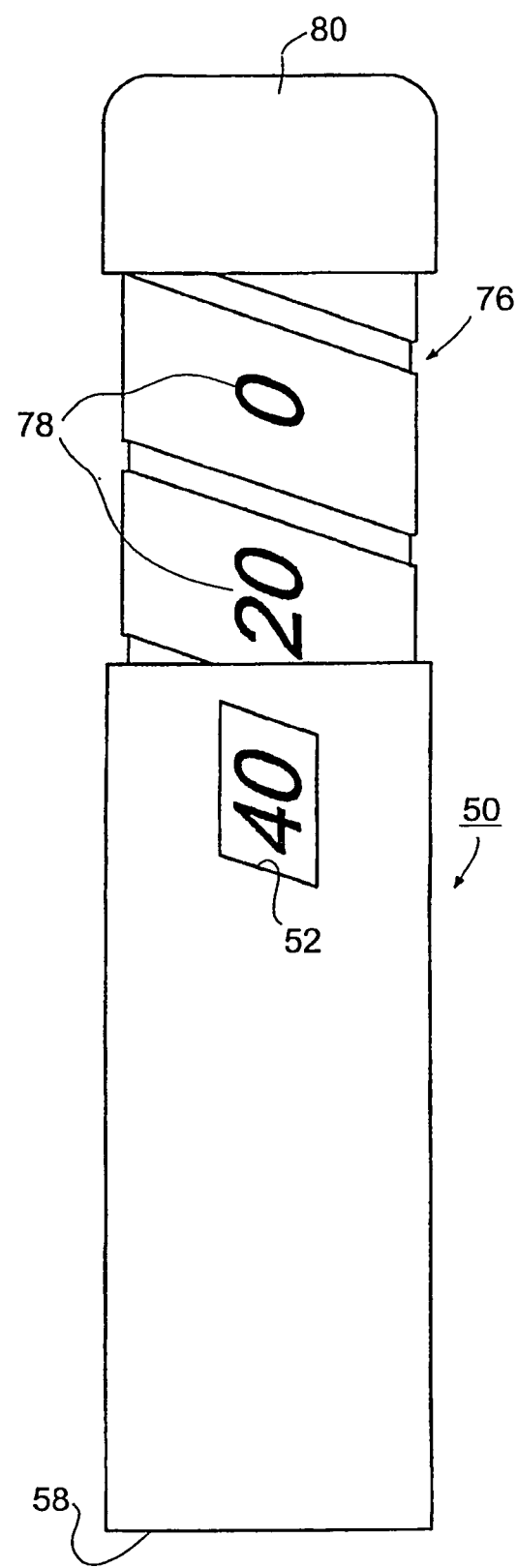
FIG. 12 is a side view analogous to FIG. 11, the injection apparatus being, however, in a position for the 40-unit dose.

FIG. 1 is a side view of a barrel 50 that has a cylindrical outer side comprising a window 52 that serves for (mechanical) display of the injection dose (see FIG. 12, where a display of 40 units is depicted as an example).

Barrel 50, made of a suitable plastic, has an external tube 54 and an internal tube 56 concentric therewith, which are joined to one another by a bridge part 58 (FIGS. 2 and 3) in such a way that an annular space 60 is formed between them. Internal tube 56 has a length that, in the exemplary embodiment, is equal to approximately four-tenths of the length of external tube 54. Its distal end is labeled 61.

Implemented in external tube 54 is an internal thread 62 that, in the exemplary embodiment, is implemented as a coarse thread having an approximately rectangular cross section of the threads, in this case (as an example) as a left-hand thread having a pitch of 10 mm per revolution (the depictions are enlarged for illustrative purposes).

Figure 2:
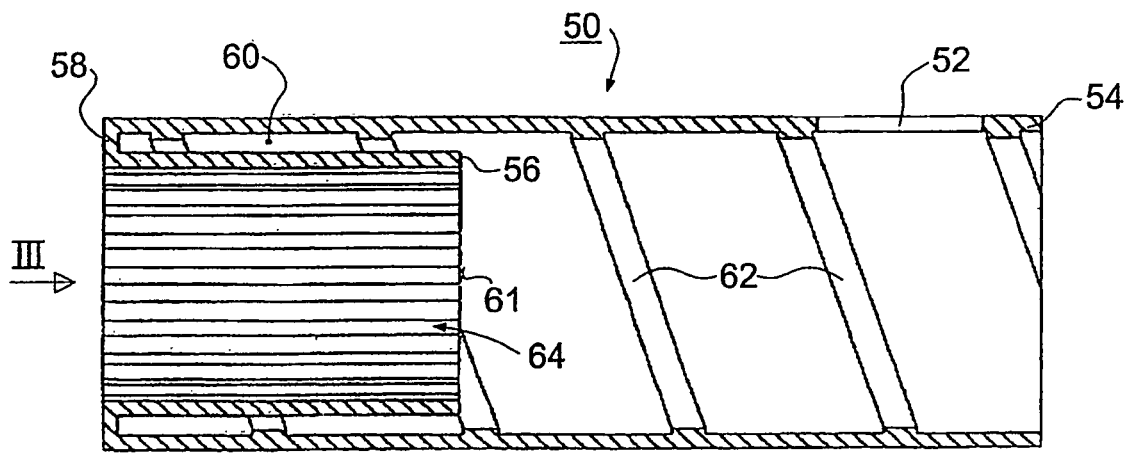
FIG. 2 is an axial section through the barrel of FIG. 1, viewed along line II-II of FIG. 3.
Figure 3:
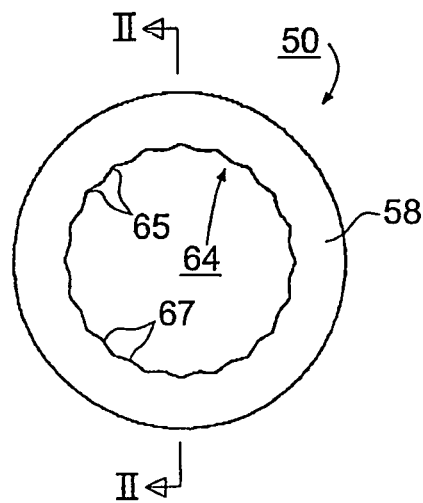
FIG. 3 is a view in the direction of arrow III of FIG. 2.
Figure 6:
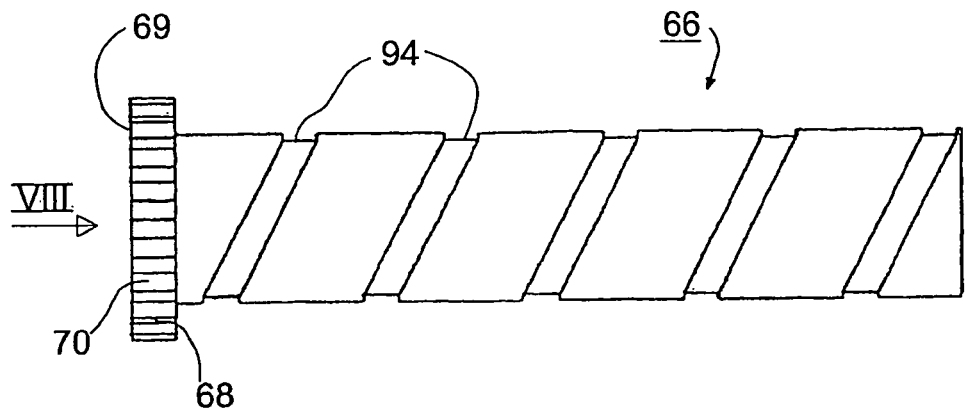
FIG. 6 is a plan view of a pushing member that, in this embodiment, is provided with an external thread.
Figure 7:
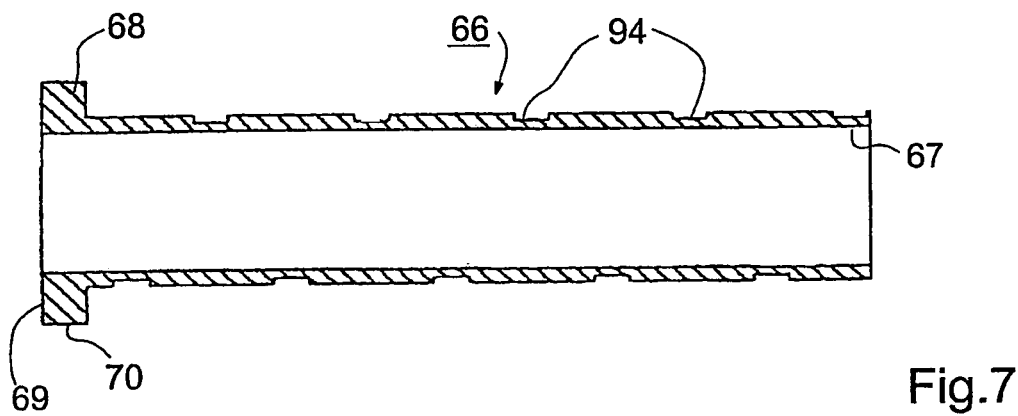
FIG. 7 is a longitudinal section through the pushing member of FIG. 6, viewed along line VII-VII of FIG. 8.
Figure 8:
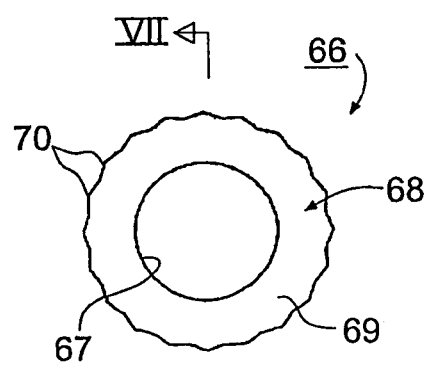
FIG. 8 is a view in the direction of arrow VIII of FIG. 6.
Figure 24:
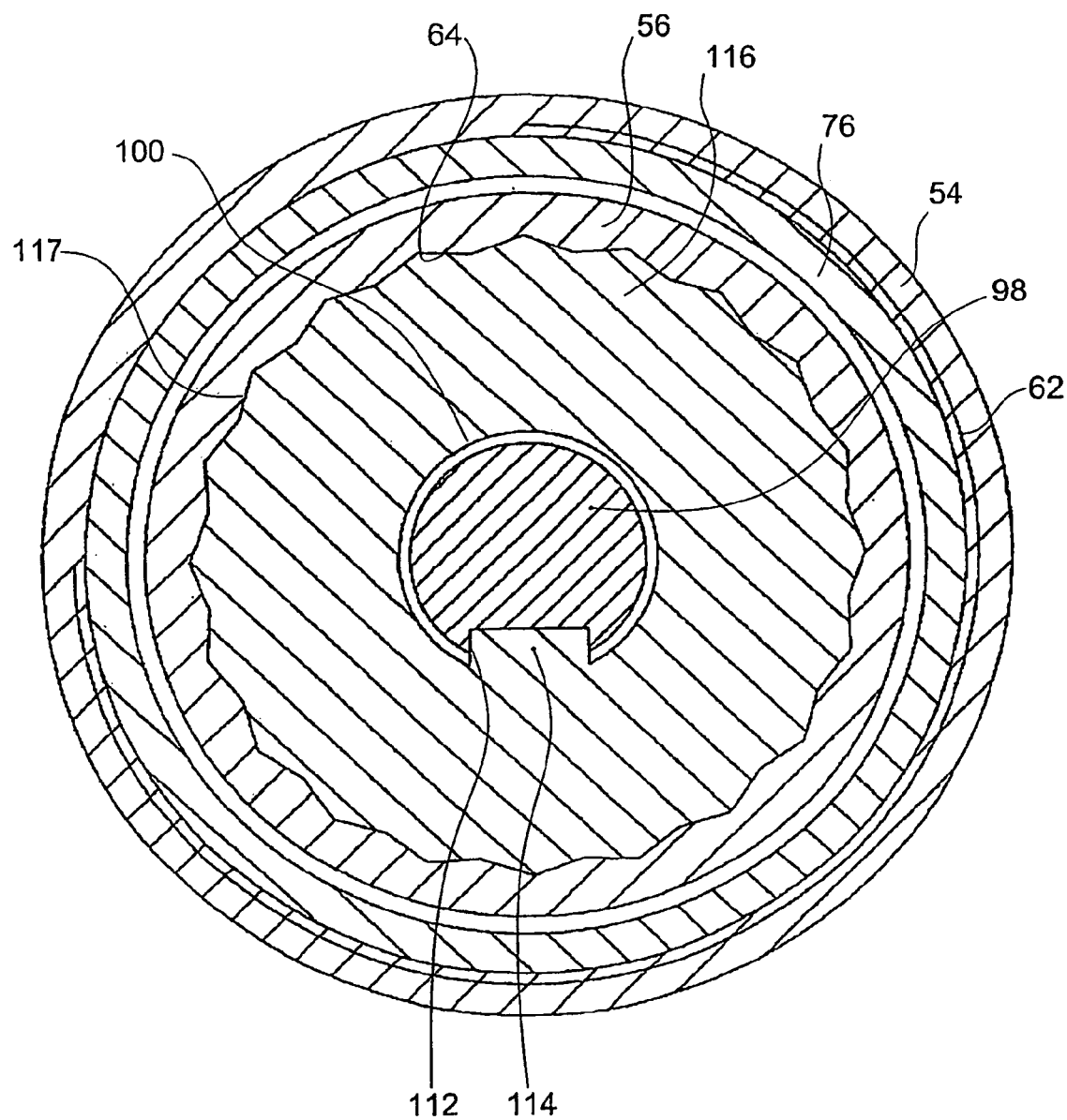
FIG. 24 is a section viewed along line XXIV-XXIV of FIG. 23.
Figure 25:
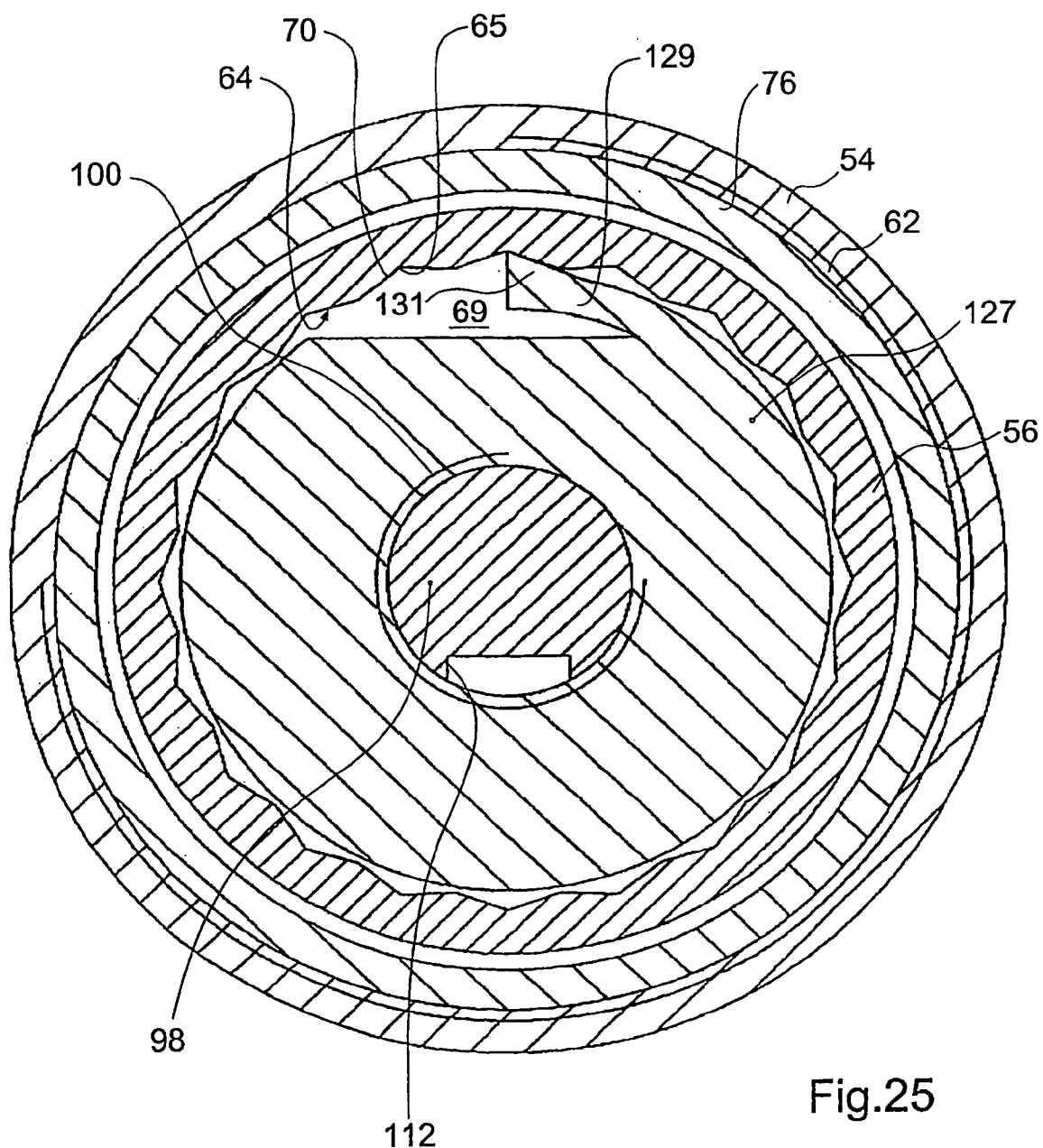
FIG. 25 is a section viewed along line XXV-XXV of FIG. 23.

Provided in this embodiment in internal tube 56 is a spline set 64 whose shape is evident from FIGS. 2 and 3. It has, in this case, twenty longitudinal grooves 65, between which are elevations 67. FIGS. 24 and 25 show spline set 64 at a greatly enlarged scale. It serves for axial guidance of a pushing member 66 that is depicted in FIGS. 6 through 8. The latter has at its proximal end a head portion 68 with an enlarged diameter, and provided on that portion is a spline set 70 that is complementary to spline set 64 and is guided therein (see, for example, FIGS. 9 and 10). The proximal end of head portion 68 is labeled 69.

External thread 74 of a setting member 76 (FIGS. 4 and 5) is guided in internal thread 62 (FIG. 2). That member has, between its threads, surfaces on which is applied a dose scale 78 ranging, for example, from "0" to "60," so that setting member 76 can also be called a "scale tube."

Figure 4:
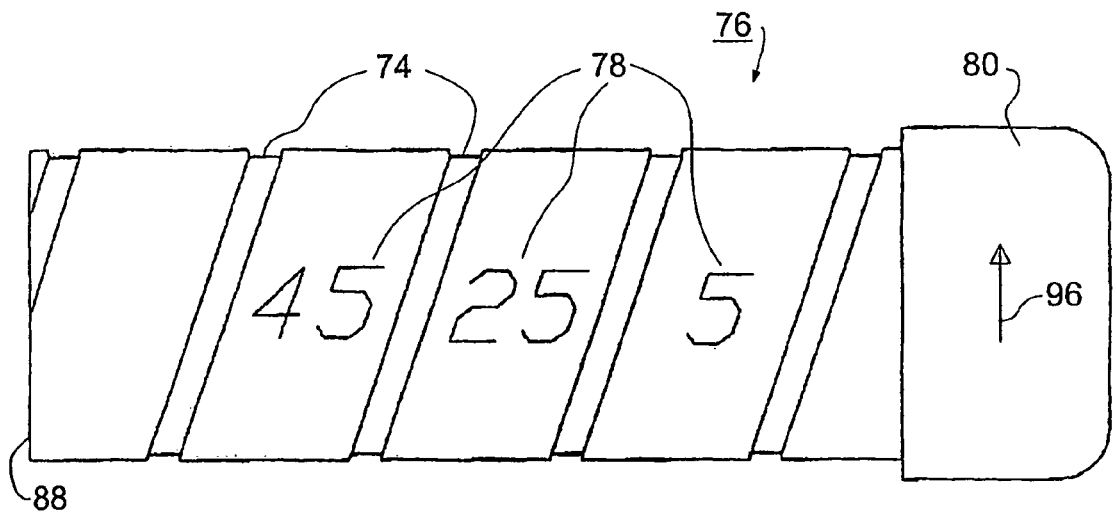
FIG. 4 is a side view of a setting member serving for dose setting, which is also referred to as a "scale tube"
Figure 5:
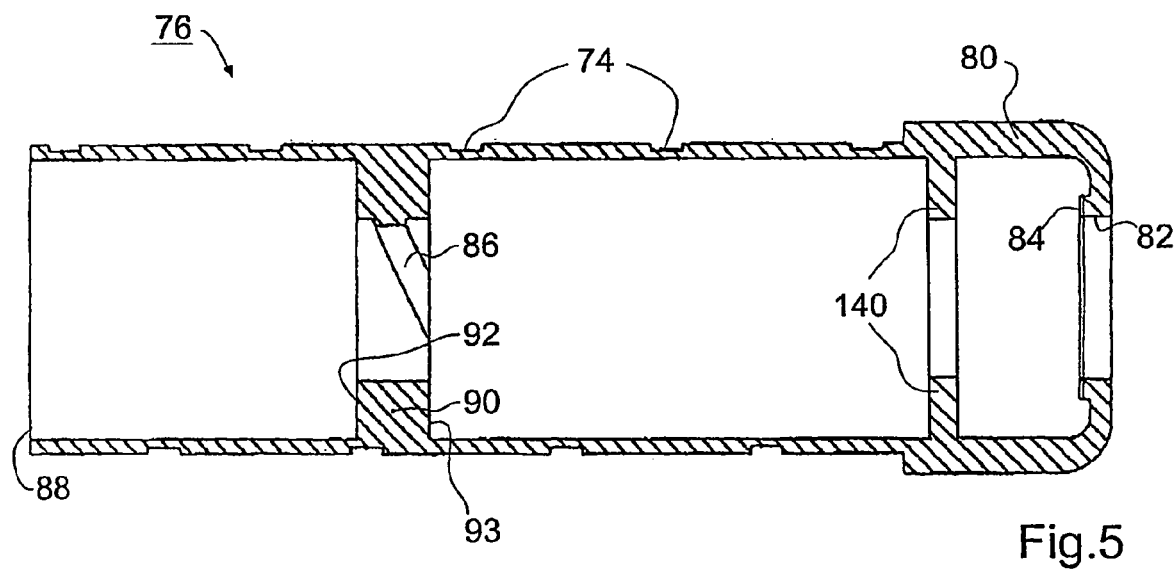
FIG. 5 is a longitudinal section through the setting member of FIG. 4.

FIG. 4 shows some of the scale numbers by way of example. Member 76 has at its distal end a setting knob 80 which serves for setting the injection dose and with which the patient injects, by axial pressure, the dose that was set (see FIG. 28 below). Provided in knob 80 is a central opening 82 at whose rim a tooth set 84 is implemented on the proximal side.

Implemented in the interior of setting member 76, on a thread carrier 90 projecting radially inward, is an internal thread 86 that is implemented here as a left-hand coarse thread having a pitch of, for example, 7 mm per revolution. Its threads preferably also have a rectangular cross section.

Figure 9:
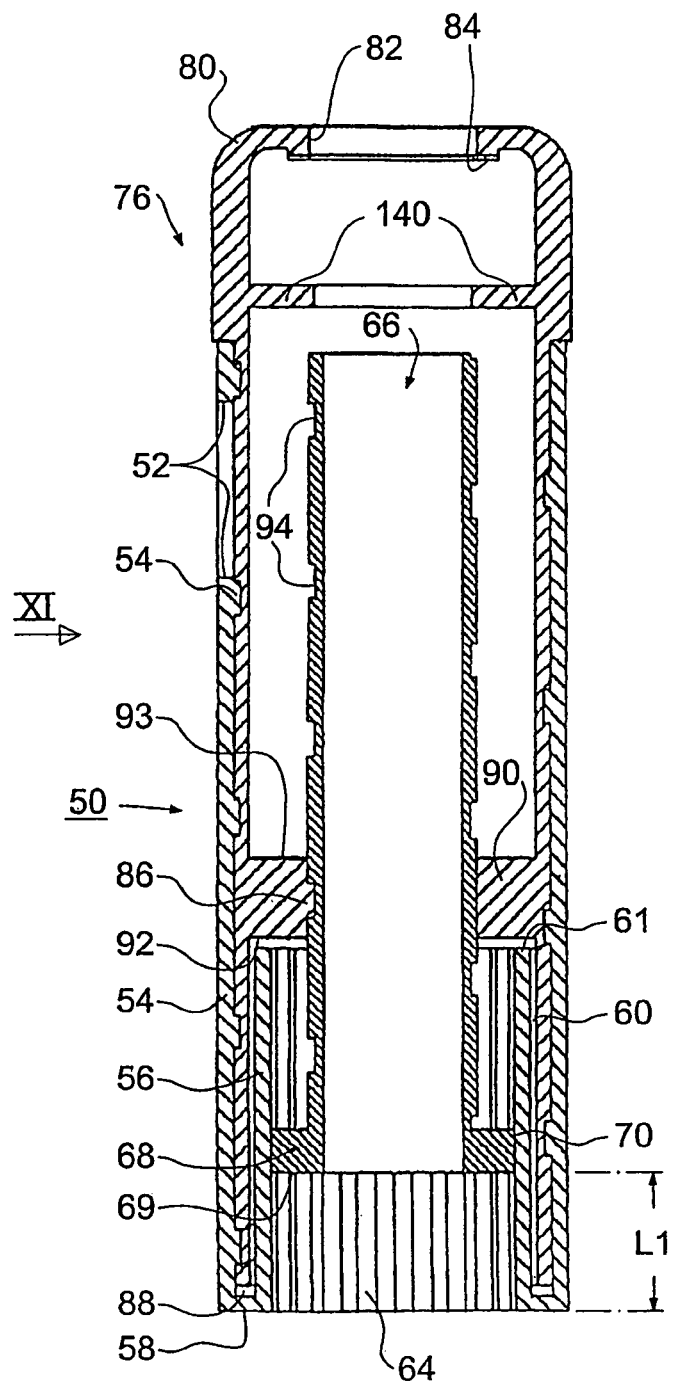
FIG. 9 is a longitudinal section through a partially assembled injection apparatus according to the invention, in its state after an injection and before an injection dose is set.

As is apparent from FIG. 9, thread carrier 90 is provided at a distance from proximal end 88 of setting member 76 such that the latter can be screwed completely into annular space 60 (FIG. 2), thread carrier 90 coming to a stop with its proximal side 92 against distal end 61 of internal tube 56. The distal side of thread carrier 90 is labeled 93.

FIGS. 6 through 8 show pushing member 66. This has an outer thread (left-hand thread) 94 that, in the assembled state (FIGS. 9 and 10), engages into internal thread 86 of setting member 76, so that a rotation of setting member 76 in which it is rotated in the direction of an arrow 96 (FIG. 4) moves setting member 76 in the distal direction, while the same rotation moves pushing member 66 in the proximal direction relative to setting member 76. Pushing member 66 has a cylindrical internal opening 67 that transitions, at the left in FIG. 7, into shoulder 69 extending radially outward.

Figure 11:
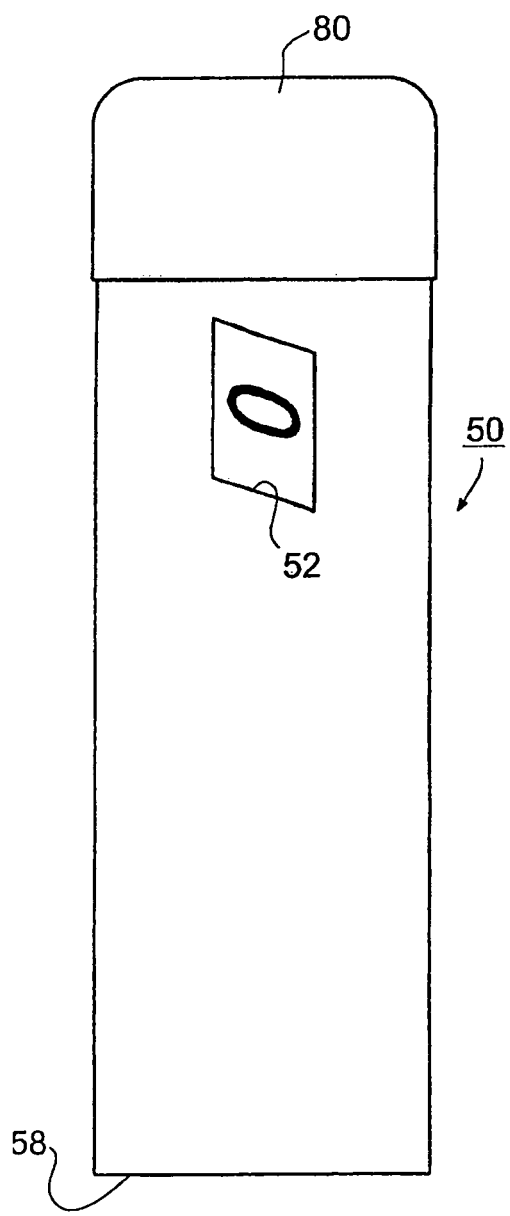
FIG. 11 is a side view in the direction of arrow XI of FIG. 9, the injection apparatus being in the position for the zero dose.

FIG. 9 shows the above-described parts prior to setting of an injection dose, the "0" dose being displayed in window 52 as shown in FIG. 11. Proximal end 69 of pushing member 66 is here at a distance L1 from the proximal end of bridge part 58.

Figure 10:
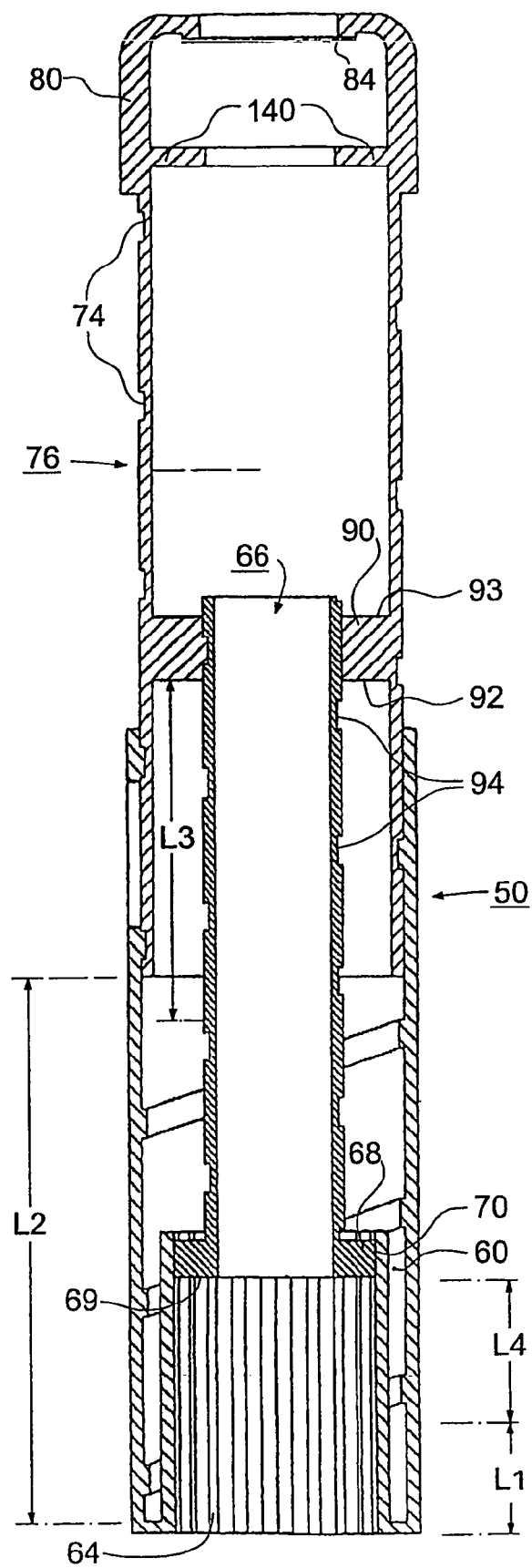
FIG. 10 is a longitudinal section through an arrangement according to FIG. 9, but after an injection dose is set.

FIG. 10 shows the parts after setting of a large injection dose, namely after three complete revolutions of setting member 76. The latter has thereby been displaced, for example, 30 mm in the distal direction. At the same time, pushing member 66 has been displaced a distance L3, for example 21 mm, in the proximal direction relative to thread carrier 90. The effect is that proximal end 69 of pushing member 66 has been displaced, as compared with FIG. 9, a distance $$L4=L2-L3 \qquad (1)$$

in the distal direction, i.e. in this case $$30-21=9 \text{ mm} \qquad (2).$$

Those 9 mm are the distance that then determines the injection dose that is injected. This is the result of the fact that pushing member 66, via its spline set 70 (FIGS. 6 and 8), is guided axially in spline set 64 of barrel 50.

With regard to pushing member 66, the same effect would result if the latter were axially guided in part 90 and were driven by an internal thread in internal tube 56. This is referred to as "kinematic reversal," i.e. the two drive connections for pushing member 66 are interchangeable. With the latter variant, the thread would need to be arranged between the outer side of part 68 and the inner side of internal tube 56, i.e. in place of axial guidance system 64, 76. The version depicted is preferred, however, because spline set 64 in the context of the present invention also has the function of a ratchet that becomes effective during dose setting.

Dose setting thus produces oppositely directed motions, i.e. setting member 76 moves rapidly in the distal direction, and pushing member 66 simultaneously moves, somewhat more slowly, relative to setting member 76 in the proximal direction; as-the final result, proximal end 69 of pushing member 66 is displaced a relatively short distance L4 in the distal direction. The arrangement according to FIGS. 9 and 10 thus acts as a linear gear linkage, and the large motion of setting member 76 has the advantage that a dose can be displayed (in window 52) with large, easily readable digits 78 (see FIGS. 11 and 12). A dose that was inadvertently set too high can also be corrected manually by turning the setting knob 80, distance L4 then becoming smaller again. In addition, the patient can accurately observe in window 52, during injection, how much he has already injected. Many patients want to have this information.

Figure 13:
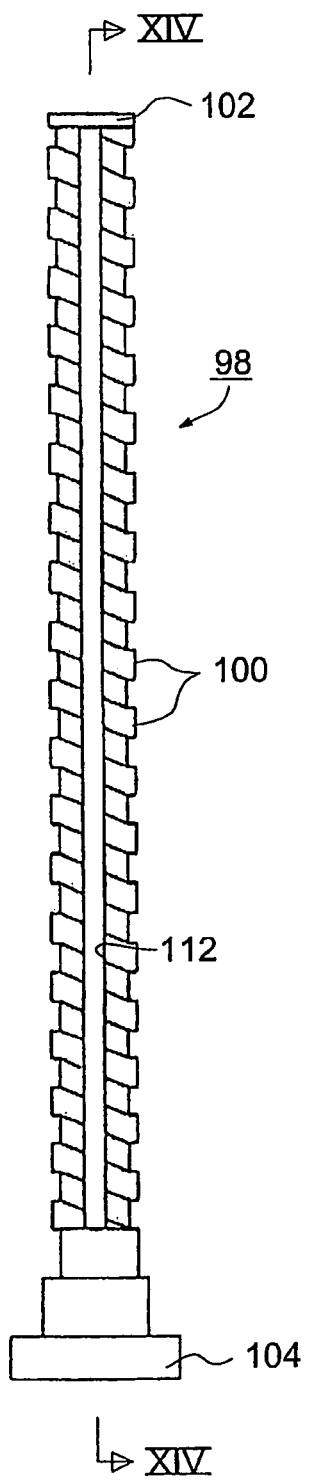
FIG. 13 is a plan view of a piston rod, provided with an external thread (left-hand thread), that serves to expel injection fluid from a container (cartridge), viewed in the direction of arrow XIII of FIG. 14.
Figure 14:
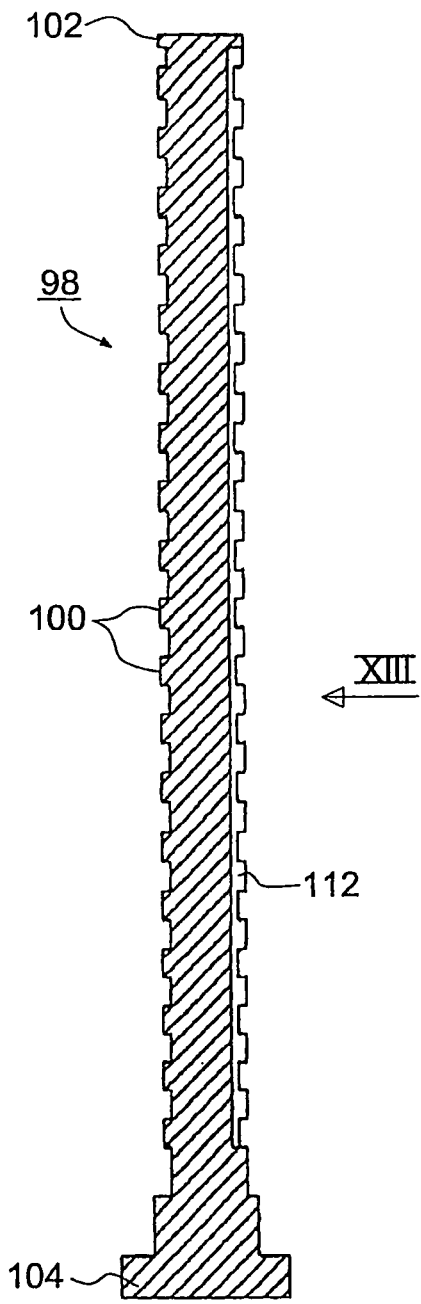
FIG. 14 is a section through the piston rod, viewed along line XIV-XIV of FIG. 13.
Figure 21:
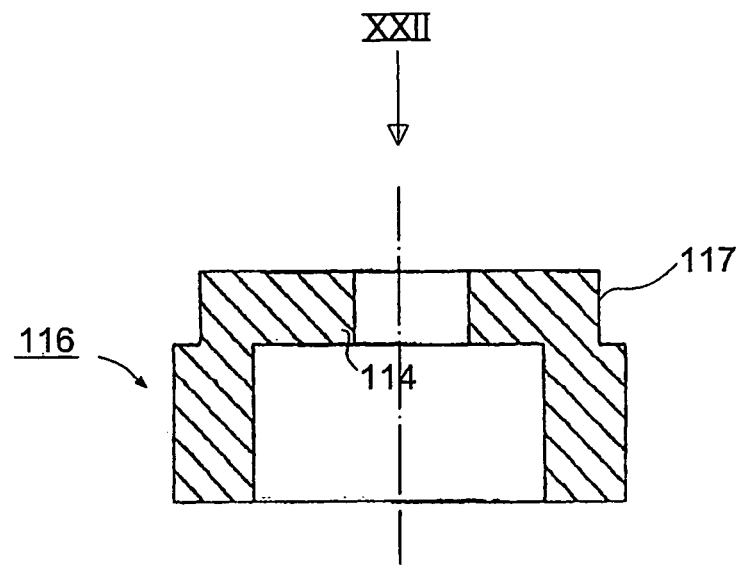
FIG. 21 is a section through a guidance member that serves for axial guidance of the piston rod in the barrel, viewed along line XXI-XXI of FIG. 22.
Figure 22:
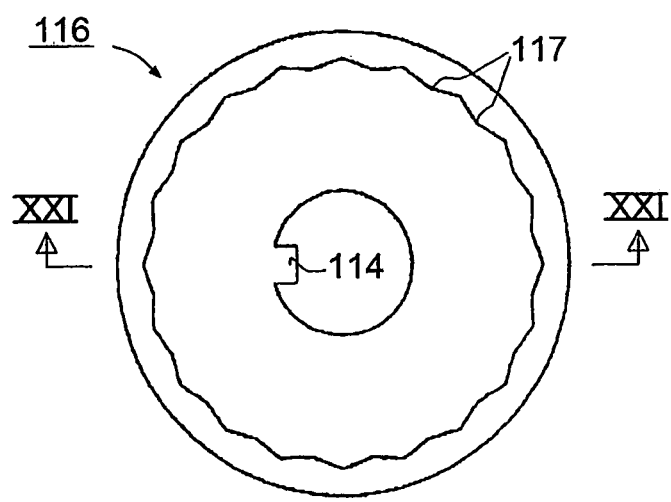
FIG. 22 is a view of the guidance member of FIG. 21 in the direction of arrow XXII of FIG. 21.
Figure 23:
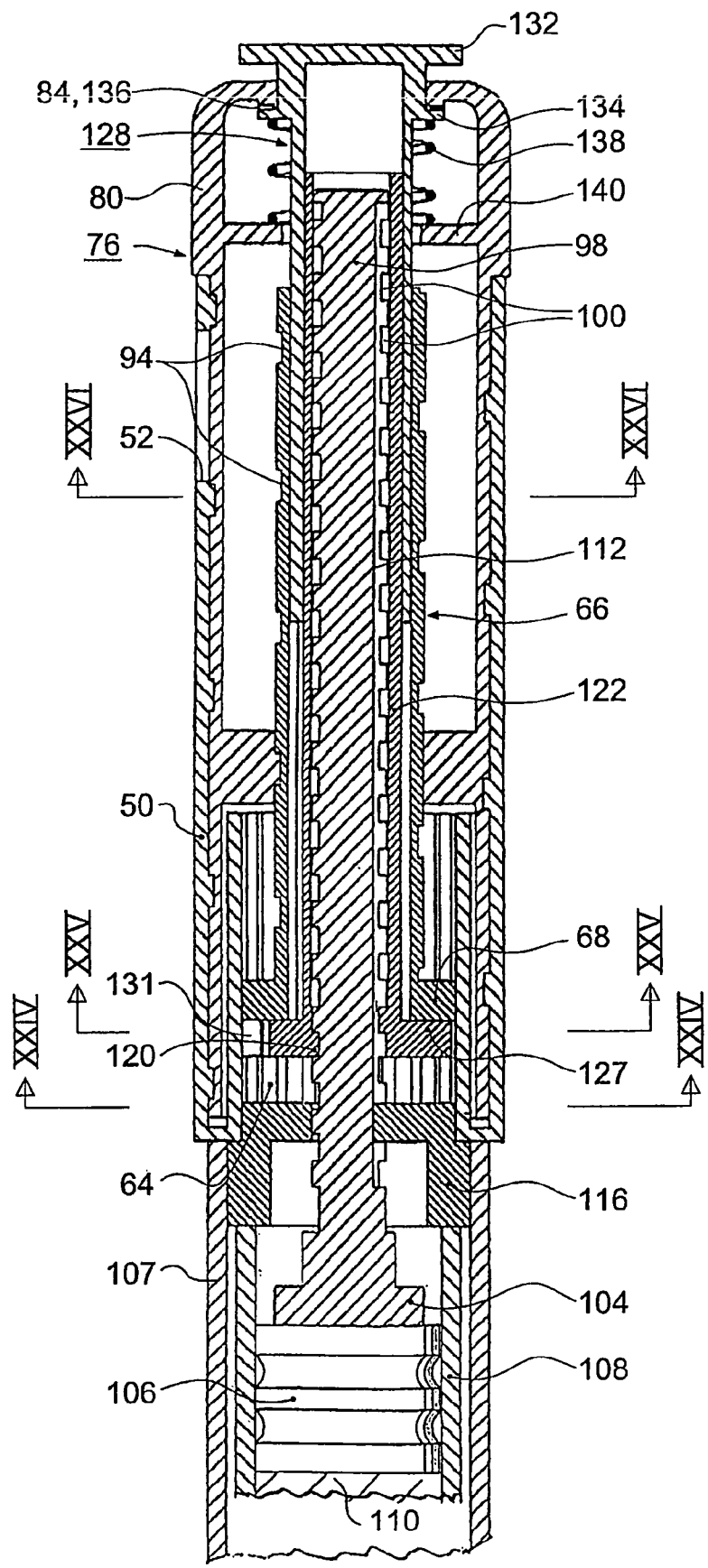
FIG. 23 is a schematic longitudinal section through an injection apparatus in the assembled state and before an injection dose is set.

FIGS. 13 and 14 show a threaded rod 98 that is provided with a rectangular coarse thread 100 that, as depicted, is a left-hand thread and has a thread pitch equal, in this example, to 3 mm per revolution. Piston rod 98 has at its distal end a stop 102 that prevents it from being screwed all the way out; and at its proximal end, i.e. at the bottom in FIGS. 13 and 14, it has a pusher plate 104 with which, in the assembled state as shown in FIG. 23, it rests against rubber piston 106 of a cartridge 108 that is filled with injection fluid 110. It additionally has a longitudinal groove 112 with which it is axially guided in a part 116 that is depicted in FIGS. 21 and 22 and that engages with a protrusion 114 into longitudinal groove 112. Part 116 has on its outer side a portion comprising a spline set 117 with which, in the assembled state, it is guided in spline set 64 of barrel 50. The result is to create an axial guidance system 112, 114 of piston rod 98 relative to barrel 50.

Part 116 as shown in FIGS. 21 and 22 fits with its external tooth set 117 into spline set 64 of barrel 50, and in the assembled state is retained in that position because, according to FIG. 23, it rests with its proximal end against the distal end of cartridge 108.

When the apparatus is opened by removing a proximal barrel part 107 from barrel part 50 (FIG. 23), part 116 is then no longer braced by cartridge 108 and can be pulled out of spline set 64 as far as a stop. It thereby becomes freely rotatable and allows piston rod 98 to be screwed in the distal direction back into its initial position, by rotation relative to thread 98. This allows a fresh, full cartridge 108 to be loaded.

During an injection, piston rod 98 displaces piston 106 in the proximal direction, i.e. downward (FIG. 23), and thereby expels injection fluid 110 from container 108. The latter can be replaced when fluid 110 is consumed. The apparatus is usually delivered empty, i.e. without a container (cartridge) 108. Piston rod 98 does not perform any rotary motion during the injection, but instead moves linearly in the proximal direction.

Figure 15:
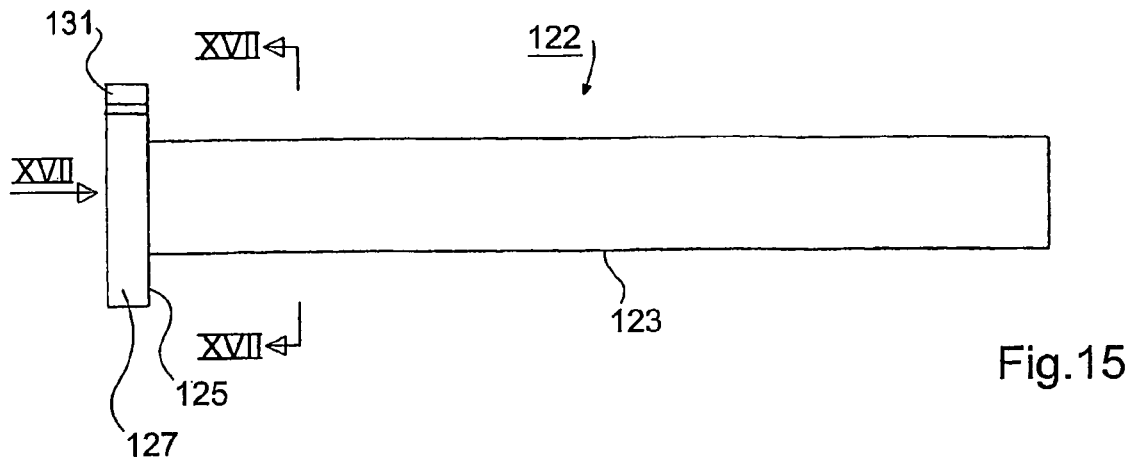
FIG. 15 is a plan view of a threaded part that is also referred to as an "advancing part"
Figure 16:
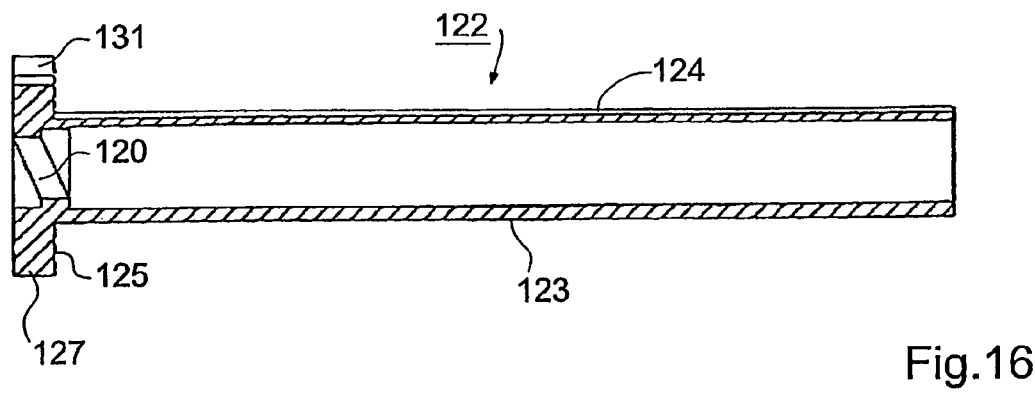
FIG. 16 is a longitudinal section through the threaded part of FIG. 15, viewed along line XVI-XVI of FIG. 17.
Figure 17:
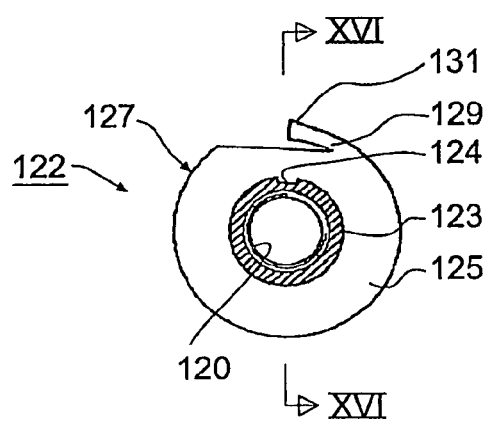
FIG. 17 is a section viewed along line XVII-XVII of FIG. 15.

External thread 100 of piston rod 98 is guided in an internal thread 120 of a threaded part 122 (FIGS. 15 through 17) that hereinafter is also referred to as the "advancing part." When threaded part 122 is rotated, it causes an axial displacement of piston rod 98 relative to this part 122. This operation is referred to as the advancing (setting) of the piston rod (98), hence the name "advancing part."

Figure 18:
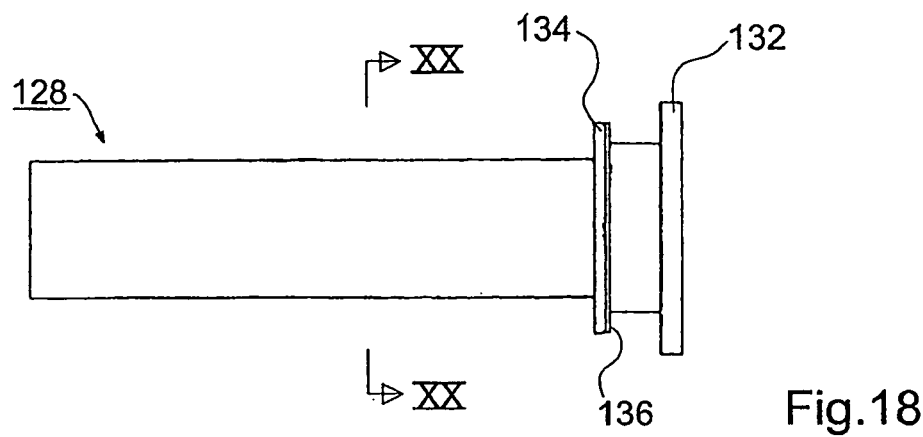
FIG. 18 is a plan view of a follower that serves, in certain operating states, to couple the threaded part (FIGS. 5 through 17) to the setting member (FIGS. 4 and 5) in such a way that said part rotates along with said member, but is freely displaceable axially relative to the setting member.
Figure 19:
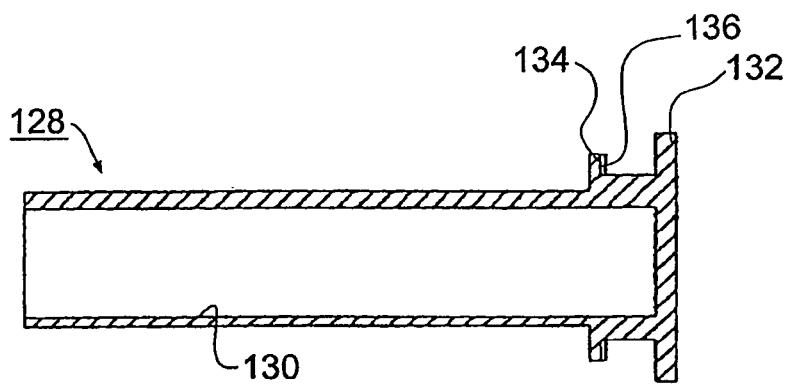
FIG. 19 is a longitudinal section through the follower of FIG. 18, viewed along line XIX-XIX of FIG. 20.
Figure 20:
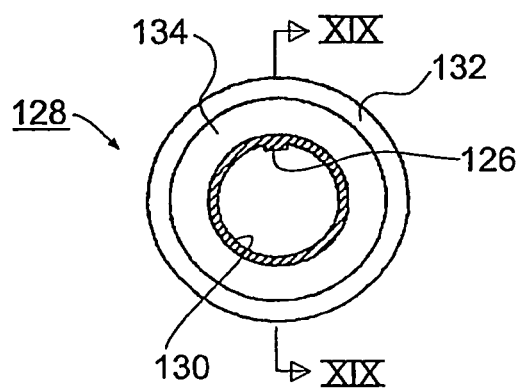
FIG. 20 is a section viewed along line XX-XX of FIG. 18.
Figure 26:
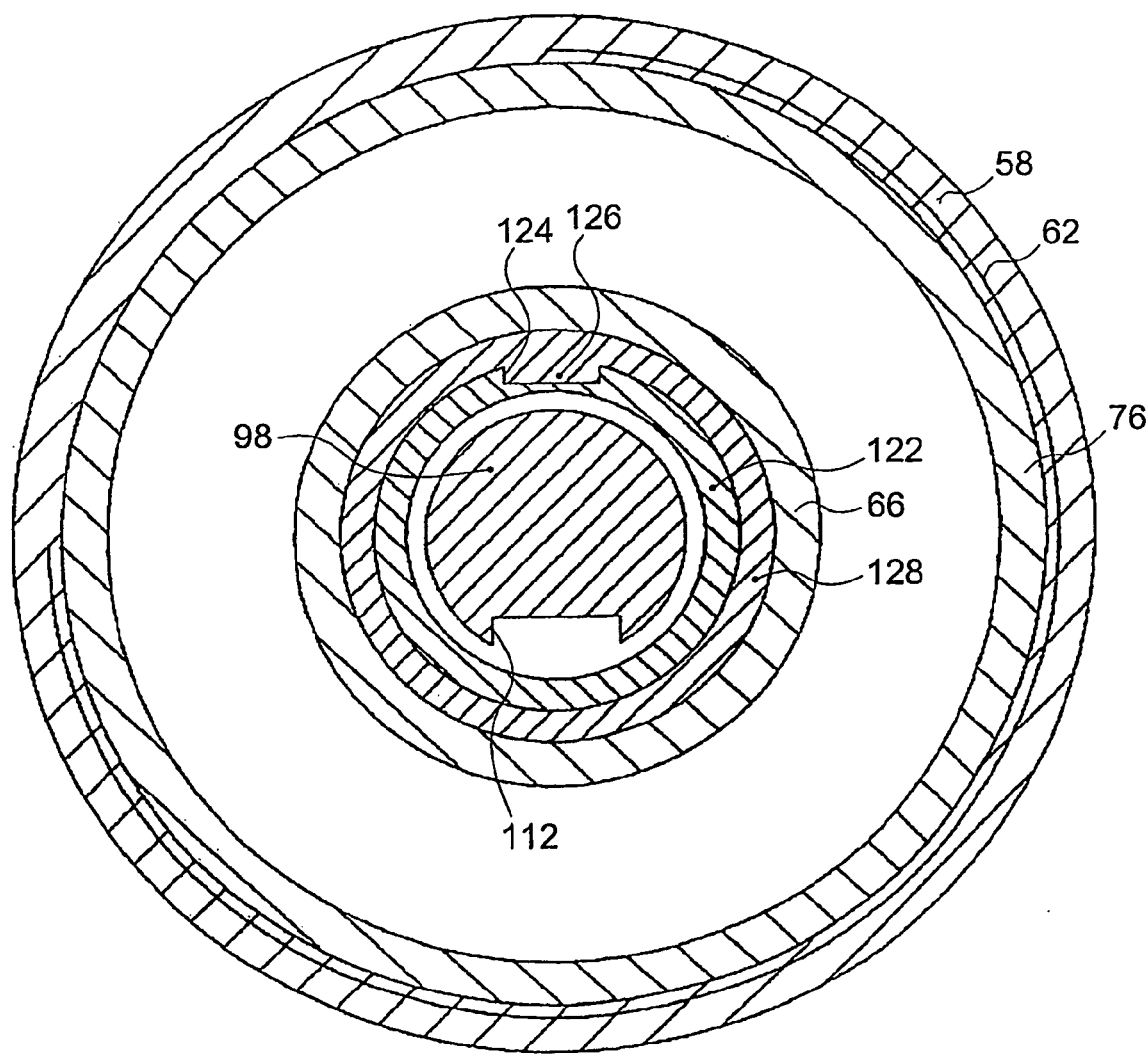
FIG. 26 is a section viewed along line XXVI-XXVI of FIG. 23.

Part 122 has on its cylindrically configured outer side 123 a longitudinal groove 124. Into this engages a radially inwardly projecting protrusion 126 (FIG. 20) of a follower 128 (FIGS. 18 through 20). The latter has a cylindrical internal opening 130 that is slidingly displaceable on cylindrical outer side 123 of threaded part 122, protrusion 126 sliding in longitudinal groove 124 and connecting parts 122, 128 non-rotatably to one another (see FIGS. 23 and 26). Cylindrical outer side 123 transitions at the left into a radially outwardly extending shoulder 125 (see FIGS. 15 through 17).

Advance member 122 has on its proximal side a head part 127 made of an elastic plastic. Head part 127 is integral with a radially resilient detent tongue 129 at whose free end is located a detent member 131 that, as shown in FIG. 25, rests with preload against axial internal spline set 64 of barrel 50 and can latch into the longitudinal grooves 65 of that spline set 64.

During an injection, head 127 along with its detent member 131 is displaced axially in spline set 64.

The coaction of detent member 131 and spline set 64 causes the patient to hear and feel twenty clicks for each revolution of setting member 76 (FIGS. 4 and 5), so that he/she can also set the dose by ear or by feel, since an audible and perceptible signal is generated for each unit. This is important because many diabetics have poor eyesight.

In addition, a dose cannot unintentionally be shifted once it has been set, since a predetermined minimum torque is necessary for any adjustment in either rotation direction.

Figure 28:
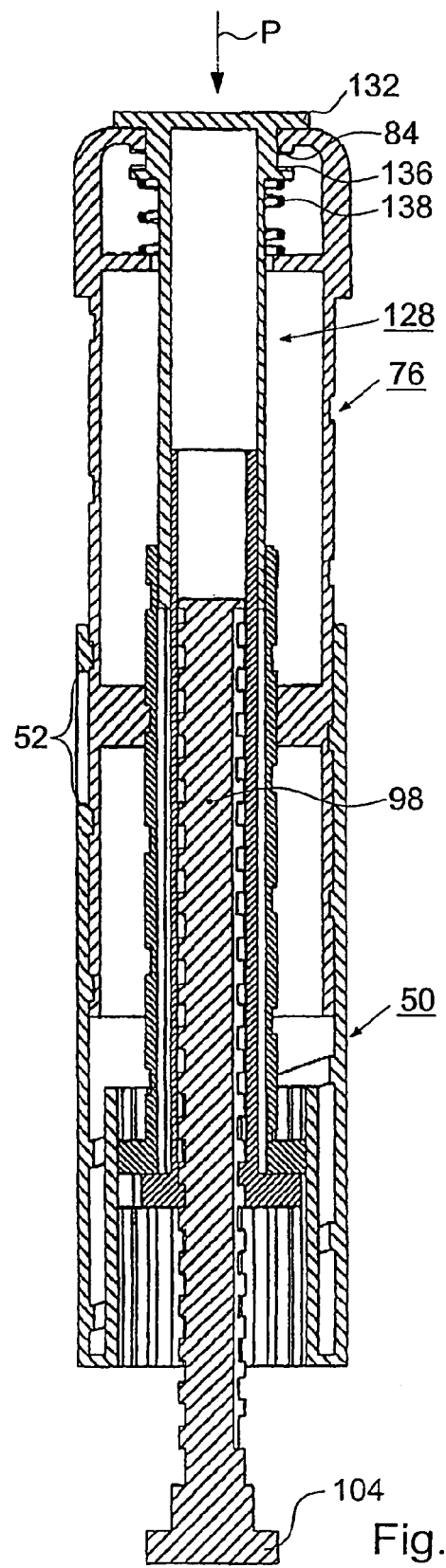
FIG. 28 is a longitudinal section analogous to FIGS. 23 and 27, but during an injection.
Figure 29:
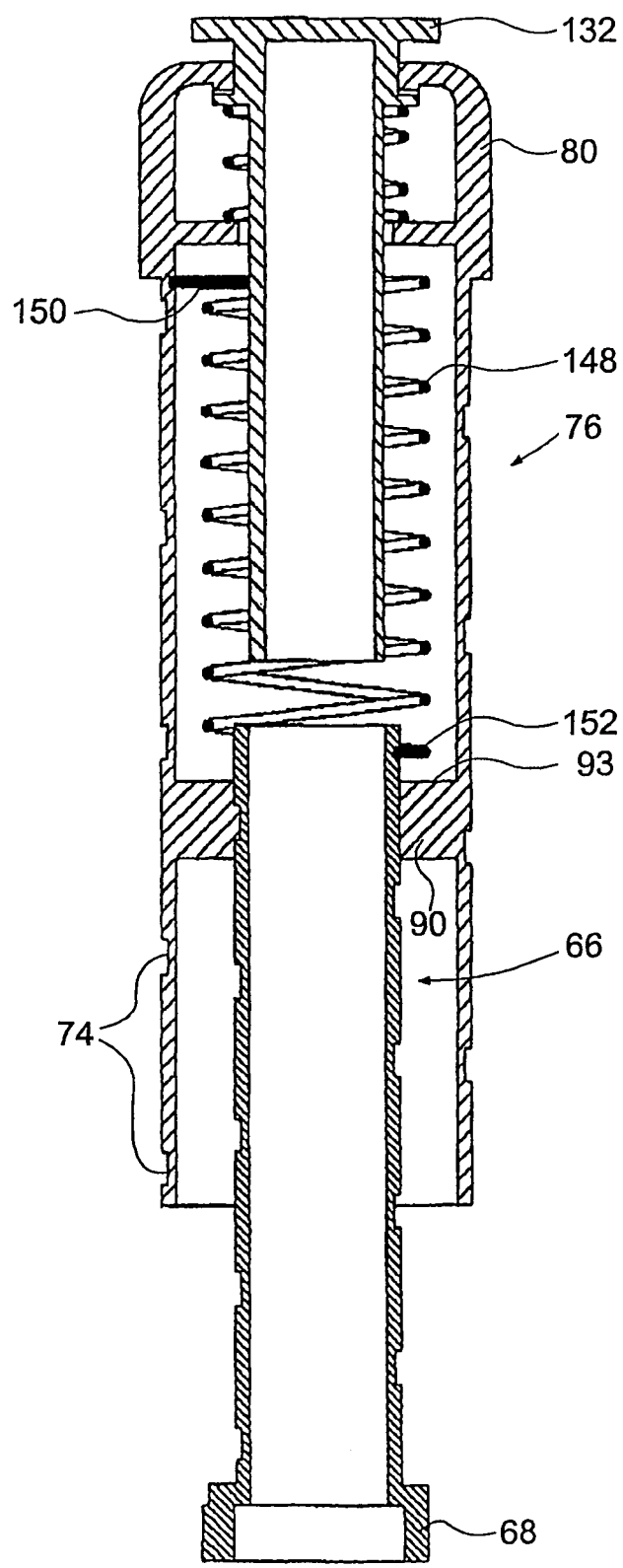
FIG. 29 shows a variant of the injection apparatus according to FIGS. 1 through 28, the injection operation being assisted by an energy that is stored in the apparatus by the user while setting the dose.
Figure 30:
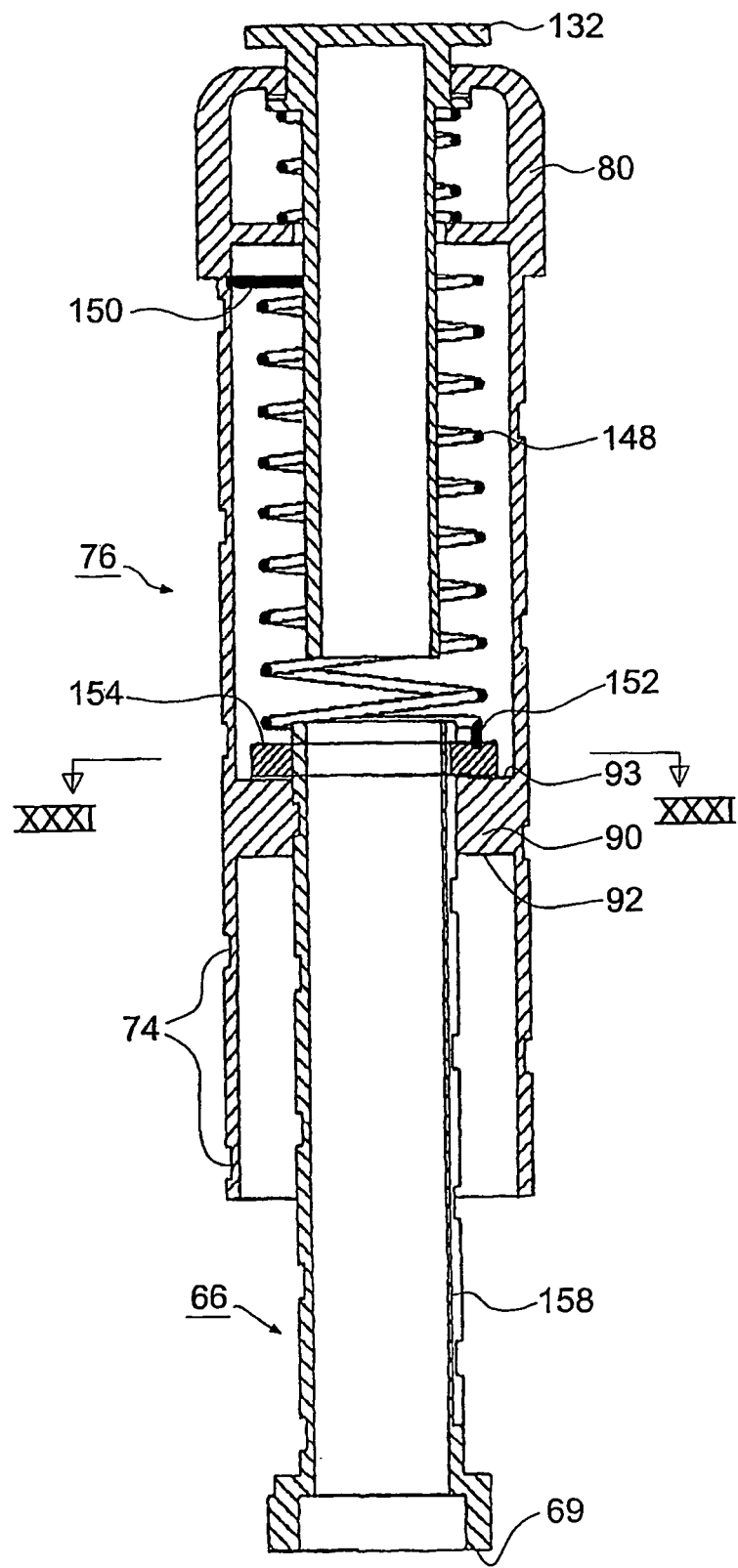
FIG. 30 shows a second variant that likewise uses the servo assistance of FIG. 29, but in which measures are taken so that the length of torsional spring 148 that is used does not change during operation.
Figure 31:
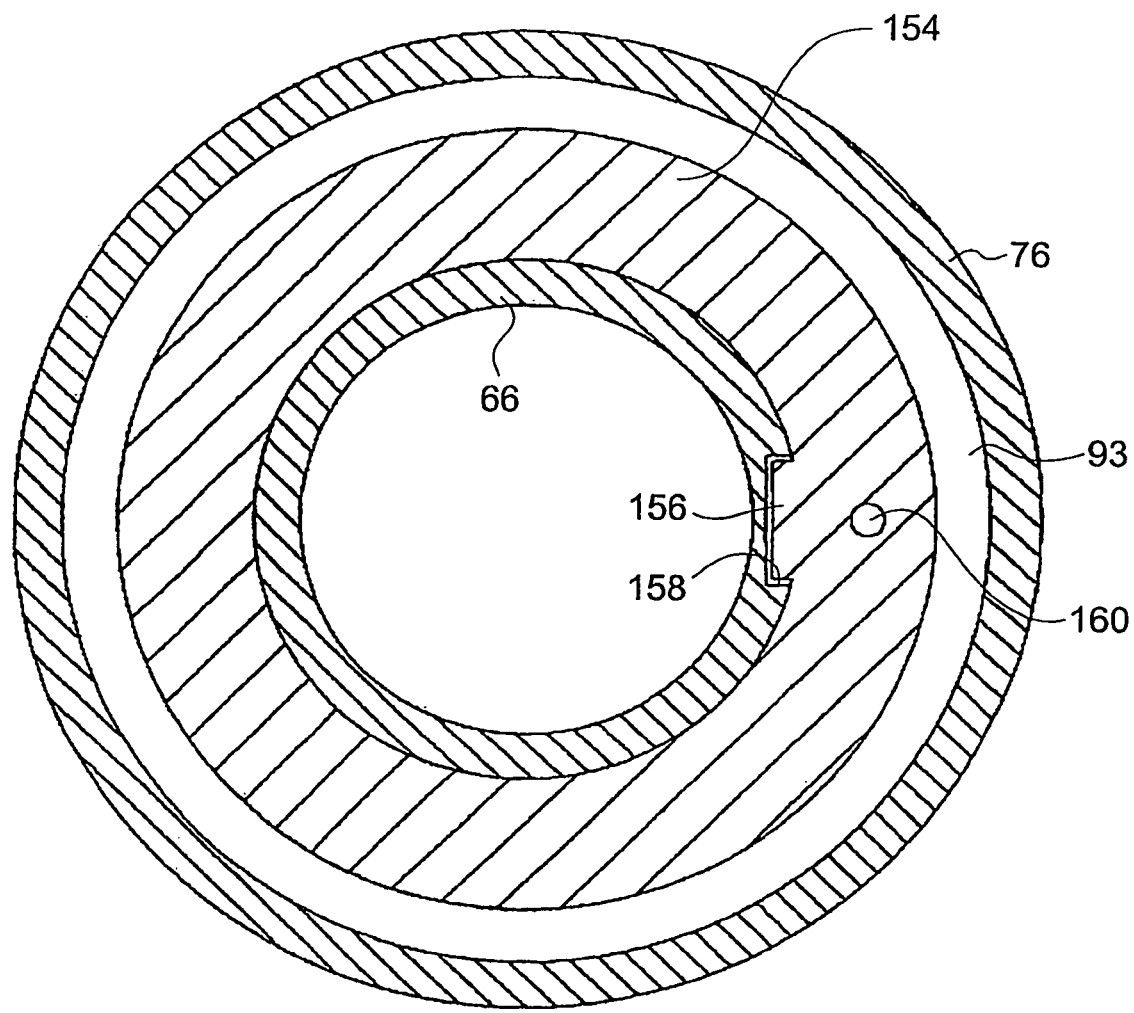
FIG. 31 is a section viewed along line XXXI-XXXI of FIG. 30.

Lastly, the coaction between detent member 131 and detent spline set 64 also means that a torsional spring 148 as shown in FIGS. 29 through 31 can become effective only when the patient presses (according to FIG. 28) on follower 128 and thereby opens coupling 84, 136, since the connection of detent member 131 to setting member 76 is then interrupted, and torsional spring 148 can consequently rotate setting member 76 or at least can assist the rotation of setting member 76.

Spline set 64 thus has several functions in the context of the exemplary embodiment, since it serves for nonrotatable connection between barrel 50 and parts that must be nonrotatably connected to it, and it also serves to create a detent connection whose function is independent of the axial position of head part 127.

Follower 128 (FIGS. 18 through 20) has at its distal end an actuation plate 132 onto which the patient presses in the proximal direction when injecting (see FIG. 28). Arranged at a distance from plate 132 is a coupling flange 134, which is equipped on its distal side, i.e. on the right in FIGS. 18 and 19, with a tooth set 136 that serves for engagement with tooth set 84 depicted in FIG. 5 and, when engaged, couples parts 76 and 128 non-rotatably to one another.

According to FIG. 23, coupling flange 134 is impinged upon in the distal direction by a compression spring 138. Spring 138 is arranged between coupling flange 134 and a support flange 140 of setting member 76, so that tooth sets 84, 136 are in engagement with one another as long as the patient does not press on actuation plate 132. When he does so, spring 138 is then compressed and tooth sets 84, 136 are brought out of engagement.

When setting an injection dose, the patient rotates setting member 76 relative to barrel 50, and in the course of that rotation follower 128 is also rotated, by way of the (closed) coupling 84, 136, through the same rotation angle relative to barrel 50. Because follower 128 is rotating, threaded part 122 also rotates (by way of guidance system 124, 128) relative to barrel 50, the previously described detent connection 64, 131 being actuated in that context.

Because, on the one hand, threaded part 122 is rotating relative to barrel 50 but, on the other hand, piston rod 98 cannot rotate relative to barrel 50 because (as shown in FIG. 24) it is axially guided by protrusion 114, piston rod 98 moves in the proximal direction relative to threaded part 122, but for the reasons described below, its position relative to barrel 50 does not change in that context.

Because setting member 76 is rotating relative to barrel 50, but pushing member 66 is not rotatable relative to barrel 50 as a result of guidance system 64, 70 (FIG. 9), pushing member 66 is displaced relative to barrel 50 in the distal direction by threads 86, 94. The distal motion of pushing member 66 relative to barrel 50 is preferably of the same magnitude as the proximal motion of piston rod 98 relative to threaded part 122.

One consequence of the proximal motion of piston rod 98 relative to threaded part 122 is that threaded part 122 is displaced distally relative to barrel 50, while piston rod 98 does not move relative to barrel 50.

(Alternatively, it would theoretically also be possible for piston rod 98 to be displaced relative to barrel 50 in the proximal direction, while threaded part 122 does not move in the axial direction, i.e. remains stationary. This is prevented, however, by the fact that threaded part 122 can easily execute a motion in the distal direction relative to barrel 50, whereas conversely a motion of piston rod 98 in the proximal direction is greatly impeded by the friction of piston 106 (FIG. 23) in container 108, so that this piston 106 acts as an abutment that prevents a motion of piston rod 98 relative to barrel 50 during the setting operation.)

The conditions occurring in the exemplary embodiment as setting member 76 was rotated through three revolutions were explained in FIG. 10. That member was, as a result, displaced upward a distance L2 =30 mm. At the same time, pushing member 66 was displaced downward a distance L3=21 mm relative to setting member 66, so that in accordance with equations (1) and (2), pushing member 66 moved a distance L4=L2−L3=30−21=9 mm upward.

With three complete revolutions of part 76, threaded part 122 (FIGS. 15 through 17) also executes three complete revolutions, thereby causing piston rod 98 in FIG. 23 to be displaced downward 9 mm, i.e. exactly the distance L4.

This means in practical terms that in FIG. 23, during a setting motion of setting member 76 (for dose-setting purposes) the location of pusher plate 104 of piston rod 98 relative to rubber piston 106 remains unchanged, i.e. piston rod 98 maintains its location relative to barrel 50 during the setting operation. A change in that location occurs only upon injection. This is a consequence of the fact that the directions and pitches of the three threads described above have a predetermined relationship to one another, and that relationship can be selected in accordance with requirements.

Figure 27:
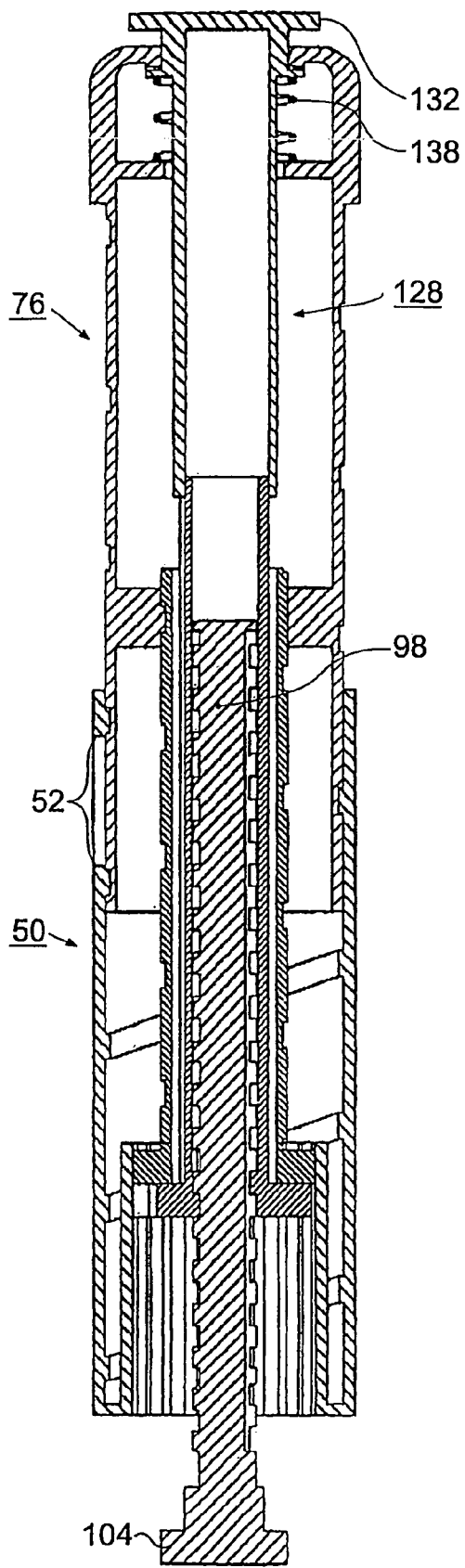
FIG. 27 is a longitudinal section analogous to FIG. 23, but after the setting of an injection dose.

FIG. 27 is an expanded depiction analogous to FIG. 10, and it is evident from it that the location of piston rod 98 has remained unchanged as compared with FIG. 23 despite the setting operation.

FIG. 28 shows an intermediate state in the course of an injection. That injection is initiated by the fact that the patient presses on plate 132 with a force P in the proximal direction. Spring 138 is thereby compressed, and coupling 84, 136 is opened.

By means of force P, optionally amplified by the torque of a torsional spring 148 described below, setting member 76 is screwed back into the position according to FIG. 9 and FIG. 23, since it has a coarse thread that automatically executes a screwing motion under axial pressure. Setting member 76 also causes pushing member 66 to be screwed back into the position shown in FIG. 9 and FIG. 23.

The location of piston rod 98 relative to threaded part 122 remains unchanged during the injection operation, and because pushing member 66 moves downward a distance L4 (FIG. 10) during that operation, threaded part 122 is displaced by pushing member 66 a distance L4 downward, i.e. in the proximal direction, since shoulder 69 of pushing member 66 pushes in the proximal direction against shoulder 125 of threaded part 122.

Piston rod 98 is thus also displaced downward a distance L4 by threaded part 122, pushing rubber piston 106 (FIG. 23) a distance L4 downward in order to expel a corresponding quantity of injection fluid 110 from cartridge 108. The result is therefore that a quantity of injection fluid corresponding to the previously set distance L4 is injected.

Because setting member 76 rotates during the injection operation, the patient can follow the sequence of the injection in window 52 as if in a movie, i.e. he knows at every moment how much he has already injected. When the number "0" appears in scale window 52, the patient knows that he has injected his entire dose.

A "0" is therefore automatically displayed in window 52 at the end of an injection (see FIG. 11) and a new setting operation can begin, so that no calculations, resetting operations, or the like are required of the patient.

FIG. 29 shows a variant in which a torsional spring 148 is arranged between setting member 76 and pushing member 66. Distal end 150 of spring 148 is nonrotatably connected to setting member 76, and proximal end 152 is nonrotatably connected to the distal end of pushing member 66.

Before an injection, the patient rotates setting member 76 and as a result screws it out of barrel 50, as described with reference to FIGS. 9 and 10. In that context, setting member 76 and pushing member 66 rotate relative to one another as described with reference to FIGS. 9 and 10. This rotation loads spring 148 torsionally; this can be reinforced by installing spring 148 with a predetermined preload.

The relative rotation between setting member 76 and pushing member 66 is reversed during an injection, and the injection apparatus returns, for example, from the position shown in FIG. 10 to the position shown in FIG. 9 as the dose that was set is injected.

The friction of piston 106 (FIG. 23) in container 108 must be overcome in this context, and this is facilitated by the energy that was stored in torsional spring 148 when setting the dose, thus making the injection easier for the patient.

As a comparison of FIGS. 9 and 10 shows, in FIG. 29 spring 148 would not only be loaded in tension but also pulled lengthwise when an injection dose is set; conversely, it would be greatly compressed during an injection, which might cause space problems.

These space problems are avoided in the version according to FIG. 30, in which a displacement member 154 is provided that slides on the cylindrical outer surface of pushing member 66. Displacement member 154 has a protrusion 156 (FIG. 31) that projects radially inward, and pushing member 66 is provided with a longitudinal groove 158 into which that protrusion 156 engages. Proximal end 158 of spring 148 engages, as depicted, into an opening 160 of displacement member 154.

By means of the force of spring 148, displacement member 154 is always held in contact against distal side 93 of thread carrier 90, so that in the variant according to FIGS. 30 and 31, the length of spring 158 does not change during dose setting and injection. As pushing member 66 is rotated, displacement member 154 also executes a corresponding rotation relative to thread carrier 90; for that reason, these parts should be manufactured from a plastic having a low coefficient of friction, or a washer made of PTFE or the like can be provided between these parts.

As already described, the energy stored in spring 148 is not released until coupling 84, 136 is opened by a pressure on plate 132 (see FIG. 28), since this interrupts the connection to detent member 131 depicted in FIG. 25; before an injection, that member retains spring 148 immovably in its tensioned position provided the detent force is sufficient therefor.

Figure 32:
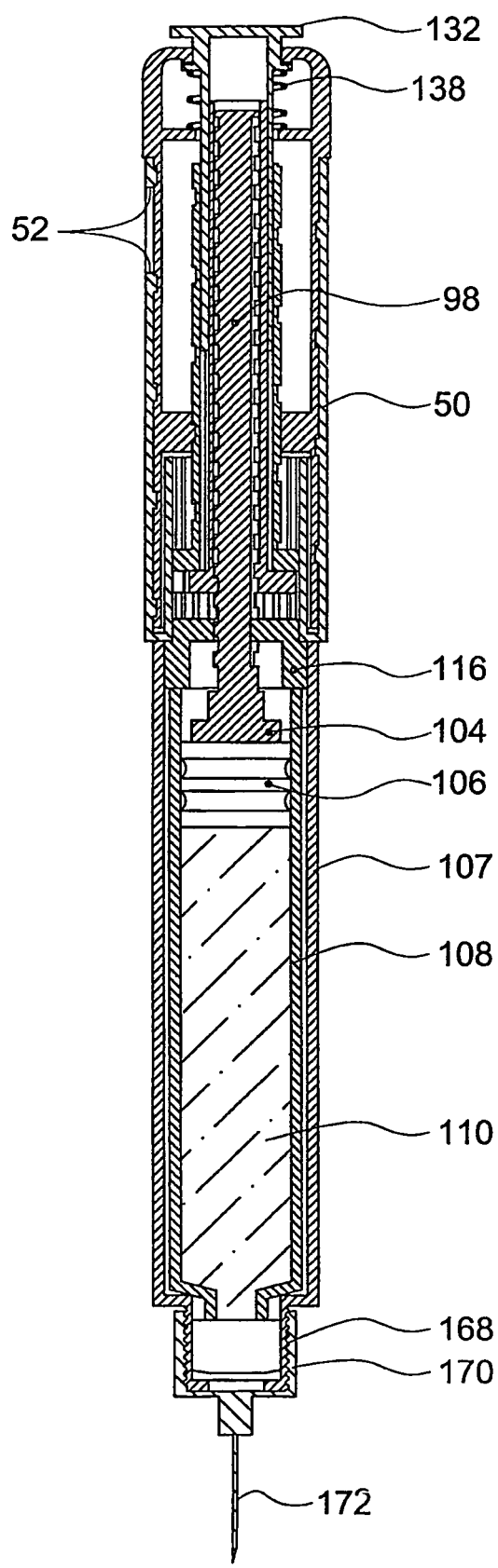
FIG. 32 is an overall depiction of the injection apparatus.

FIG. 32 is an overall depiction of the injection apparatus. The upper, distal part corresponds to the depiction in FIG. 23, to which the reader may therefore be referred. Cartridge 108 is guided in proximal barrel part 107. The latter has at the bottom a thread 168 for screwing on threaded part 170 of a needle 172 whose distal part, in known fashion, pierces a rubber membrane (not depicted) of cartridge 108 and thereby creates a connection between needle 172 and injection fluid 110 in cartridge 108, as is known to one skilled in the art. Needle 172 is usually replaced before each injection.

Many variants and modifications are, of course, possible in the context of the present invention.

The invention claimed is:

1. An injection apparatus comprising:
    a housing (50) configured to receive a container (108) containing injection fluid (110);
    a piston rod (98) having a longitudinal axis (112, 114) and being provided with a thread (100), said piston rod (98) serving, in operation, for expelling injection fluid (110) from such a container (108), and being non-rotatably guided relative to the housing (50) for movement in the direction of the longitudinal axis (112, 114) thereof
    a threaded part (122) formed with a first thread (120) which is in engagement with the thread (100) of the piston rod (98), the position of the threaded part (122) relative to the housing (50) being adjustable;

a setting member (76) provided for setting an injection dose by rotation of said setting member (76);

a coupling (84, 136) arranged between the setting member (76) and the threaded part (122), said coupling (76) being closed during setting of the injection dose and open during an injection process so that the threaded part (122) is, for setting an injection dose, rotatable relative to the piston rod (98) and relative to the housing (50) and moves in the direction of the longitudinal axis (112, 114) and relative to the piston rod (98) and relative to the housing (50) during a dose-setting operation, and moves, during an injection process, axially relative to the housing (50) in an injection direction but is hindered against rotation relative to the piston rod (98), the setting member (76) being so rotatable arranged in the housing (50) that, for setting an injection dose, a combined length of the housing (50) and the setting member (76) is adjustable, from an initial combined length value, by a rotation of said housing and said setting member with respect to each other, said combined length being resettable, during an injection process, to said initial combined length value by rotating said housing (50) and said setting member (76) with respect to each other;

a pushing member (66) being provided, which is connected to the housing (50) via a first drive connection (64, 70) and to the setting member (76) via a second drive connection (86, 94), so that the pushing member (66) moves relative to the housing in a predetermined direction when the setting member (76) is moved, likewise in that predetermined direction, by rotation relative to the housing (50) and pushes said threaded member (122) and said piston rod (98) in an injection direction during an injection process.

2. The injection apparatus according to claim 1, wherein the second thread (86, 94) is implemented as a second drive connection for the pushing member (66).

3. The injection apparatus according to claim 1, wherein the thread pitches of the first, second, and third threads are dimensioned such that, during the setting operation, a rotation of the setting member (76) has substantially no influence on the location of the piston rod (98) relative to the housing (50).

4. The injection apparatus according to claim 1, further comprising
a torsional spring (148), which is arranged in such a way that energy is stored in it when a dose is set, and energy is released from it during an injection operation.

5. The injection apparatus according to claim 4, wherein the torsional spring (148) is arranged between the setting member (76) and the pushing member (66), a relative rotation between those parts modifying the torque generated by the torsional spring (148).

6. The injection apparatus according to claim 5, wherein the torsional spring (148) is joined nonrotatably but axially displaceably to the pushing member (66).

7. The injection apparatus according to claim 1, wherein a detent connection (64, 131) is provided between the housing (50) and a part (122) connectable via a controllable coupling (84, 136) to the setting member (76).

8. The injection apparatus according to claim 7, wherein there is provided, in the housing (50), a spline set (64) that coacts with a detent member (131) that is axially displaceable relative to the barrel housing (50), in order to produce rotational detent positions that are independent of the relative axial locations of the detent member (131) and housing (50).

9. The injection apparatus according to claim 8, wherein the detent connection (64, 131) is implemented in such a way that, by means of a first predetermined minimum torque, it is adjustable in a rotation direction that increases the injection dose, and by means of a second predetermined minimum torque, it is adjustable in a rotation direction that decreases the injection dose.

10. The injection apparatus according to claim 7, wherein the detent connection (64, 131) is implemented in such a way that, by means of a first predetermined minimum torque, it is adjustable in a rotation direction that increases the injection dose, and, by means of a second predetermined minimum torque, it is adjustable in a rotation direction that decreases the injection dose.

11. The injection apparatus according to claim 10, wherein the first and the second predetermined minimum torques are of substantially equal magnitude.

12. The injection apparatus according to claim 1, wherein a follower (128) is provided, coupled to said setting member (76) in such a way that a dose-setting rotation of the setting member (76) is transmitted to the follower, but a rotation of the setting member occurring during an injection is not transmitted to the follower (128).

13. The injection apparatus according to claim 12, wherein said threaded part (122) is connected to said follower (128) in such a way that a rotation of the follower (128) is transmitted to the threaded part (122), but an axial displacement of the follower (128), relative to the housing (50), is not transmitted to the threaded part.

14. The injection apparatus according to claim 12, wherein the pushing member (66) is provided on its patient-proximal side with a contact member (69) which is configured for contact against a patient-remote side (125) of the threaded part (122) in order, during an injection, to displace the piston rod (98) via the threaded part (122) in a patient-proximal direction, and to expel injection fluid (110) from the container (108).

15. The injection apparatus according to claim 1, wherein said first drive connection is configured as a second thread (86, 94), and
said second drive connection is configured as an axial guide (64, 70).

16. The injection apparatus according to claim 15, further comprising
a third threaded connection (62, 74), arranged between said housing (50) and said setting member (76), serving for length adjustment purposes.

17. The injection apparatus according to claim 16, wherein portions of the setting member (76) that are located adjacent the third thread (62, 74) are provided with scale values (78) for displaying the injection dose that is set.

18. The injection apparatus according to claim 17, wherein the housing (50) is provided with a window (52) for displaying at least one of the scale values (78).

19. The injection apparatus according to claim 16, wherein the second thread (86, 94) and the third thread (62, 74) have identical thread directions.

20. The injection apparatus according to claim 19, wherein the thread pitch of the third thread (62, 74) is greater in absolute value than the thread pitch of the second thread (86, 94).

21. The injection apparatus according to claim 19, wherein the thread direction of the first thread (100, 120) corresponds to that of the third thread (62, 74).

22. The injection apparatus according to claim 21, wherein the thread pitch of the first thread (100, 120) is smaller in absolute value than the thread pitch of the third thread (62, 74).

23. The injection apparatus according to claim 22, wherein said coupling (84, 136), is controllable between an open state and a closed state and, in said closed state, enables transfer of torque from the setting member (76) to the follower (128).

24. The injection apparatus according to claim 23, wherein the controllable coupling (84, 136) is so configured that it transfers the rotational motion of the setting member (76) to the follower (128) during the setting of an injection dose.

25. The injection apparatus according to claim 23, wherein the controllable coupling (84, 136) is so configured that it does not transfer a rotational motion of the setting member to the follower (128) during an injection.

26. The injection apparatus according to claim 23, wherein the controllable coupling (84, 136) is controllable by the injection operation in such a way that, after completion of an injection, said coupling returns to a closed state, and remains closed during dose-setting, so that a dose-setting rotation of the setting member (76) is transferred to the threaded part (122) by the controllable coupling (84, 136).

27. The injection apparatus according to claim 23, wherein the controllable coupling (84, 136) is implemented so that it opens during a component movement occurring at the beginning of an injection.

28. The injection apparatus according to claim 16, wherein the respective thread pitches or steepnesses of said first, second and third threaded connections are selected such that, during setting of an injection dose, the displacement of the pushing member (66) in a predetermined direction is at least as large as the displacement of said threaded part (122) in said predetermined direction.

* * * * *